United States Patent

Tsuji et al.

Patent Number: 5,723,260
Date of Patent: Mar. 3, 1998

[54] UNSATURATED GROUP-CONTAINING URETHANE COMPOUND, PHOTOPOLYMERIZABLE COMPOSITION CONTAINING IT, AND PHOTOSENSITIVE LITHOGRAPHIC PRINTING PLATE

[75] Inventors: Shigeo Tsuji; Hiroshi Tomiyasu, both of Yokohama, Japan

[73] Assignee: Mitsubishi Chemical Corporation, Tokyo, Japan

[21] Appl. No.: 715,088

[22] Filed: Sep. 17, 1996

[30] Foreign Application Priority Data

Sep. 18, 1995 [JP] Japan .................... 7-238552

[51] Int. Cl.$^6$ .................... G03F 7/027; G03F 7/029; G03F 7/09; C07C 261/00
[52] U.S. Cl. .................... 430/278.1; 430/924; 430/947; 430/284.1; 522/92; 522/95; 522/90; 522/26; 560/115
[58] Field of Search .................... 560/220, 115; 430/284.1, 278.1, 947, 924; 522/92, 95, 90, 26

[56] References Cited

U.S. PATENT DOCUMENTS

| | | | |
|---|---|---|---|
| 4,002,669 | 1/1977 | Gross et al. | 560/220 |
| 4,458,007 | 7/1984 | Geissler et al. | 522/95 |
| 5,476,749 | 12/1995 | Steinmann et al. | 430/284.1 |

FOREIGN PATENT DOCUMENTS

| | | |
|---|---|---|
| 0 614 122 | 9/1994 | European Pat. Off. . |
| 0 638 547 | 2/1995 | European Pat. Off. . |
| 57-128716 | 8/1982 | Japan . |
| 61-181872 | 8/1986 | Japan .................... 522/90 |
| 63-202740 | 8/1988 | Japan . |

Primary Examiner—Cynthia Hamilton
Attorney, Agent, or Firm—Oblon, Spivak, McClelland, Maier & Neustadt, P.C.

[57] ABSTRACT

An unsaturated group-containing urethane compound of the following formula (I):

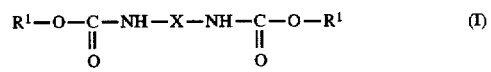

wherein X is a $C_{1-20}$ alkylene group which may be branched, and $R^1$ is a group of the following structural formula (A) or (B):

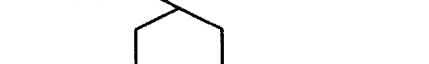

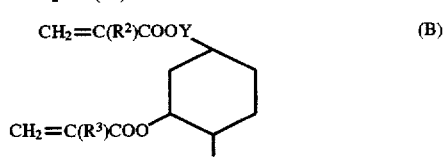

wherein each of $R^2$ and $R^3$ which are independent of each other, is a hydrogen atom or a methyl group, and Y is a $C_{1-6}$ alkylene group which may be branched.

9 Claims, No Drawings

UNSATURATED GROUP-CONTAINING URETHANE COMPOUND, PHOTOPOLYMERIZABLE COMPOSITION CONTAINING IT, AND PHOTOSENSITIVE LITHOGRAPHIC PRINTING PLATE

The present invention relates to a novel urethane compound having polymerizable unsaturated groups, a photopolymerizable composition containing it and photosensitive lithographic printing plate. More particularly, it relates to a urethane compound which, when incorporated in a photopolymerizable composition as an unsaturated group-containing monomer component, is capable of improving the properties of the composition such as the sensitivity, adhesion to a substrate and storage stability, a photopolymerizable composition employing it and a photosensitive lithographic printing plate.

Various compounds having urethane bonds and photopolymerizable unsaturated groups, are known and have, heretofore, been used for production of photosensitive recording materials such as printing plates or photoresists. For example, Japanese Unexamined Patent Publication No. 202740/1988 discloses an urethane compound which is a reaction product of an alkyl diisocyanate, a dihydric alcohol and a mono(meth)acrylate of a dihydric alcohol, and Japanese Examined Patent Publication No. 32293/1990 discloses a urethane compound which is a reaction product of glycerol di(meth)acrylate with a diisocyanate. However, photosensitive recording materials produced by using such conventional polymerizable urethane compounds, have various drawbacks, and a composition excellent in all of the sensitivity, adhesion to a substrate and storage stability, is desired.

The present invention is intended to provide a polymerizable compound which is capable of presenting a photopolymerizable composition excellent in all of the sensitivity, adhesion to a substrate and a developability, when used as a polymerizable monomer contained in the photopolymerizable composition, and a photopolymerizable composition and a photosensitive lithographic printing plate employing it.

Namely, it is an object of the present invention to provide an urethane compound having a novel structure, as a novel substance.

Another object of the present invention is to provide a photopolymerizable monomer consisting of the novel urethane compound.

A further object of the present invention is to provide a photopolymerizable monomer and a photopolymerizable composition which is highly sensitive to visible light and which is excellent in the storage stability.

Another object of the present invention is to provide a photopolymerizable composition which is highly sensitive to visible light and which is excellent in the storage stability and adhesion to a substrate.

Another object of the present invention is to provide a photosensitive lithographic printing plate which is excellent in the balance of the sensitivity and the developability.

Still another object of the present invention is to provide a photosensitive lithographic printing plate which is excellent in all of the sensitivity, storage stability, printing resistance and developability.

Such objects of the present invention can be accomplished by an unsaturated group-containing urethane compound of the following formula (I):

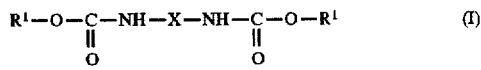

wherein X is a $C_{1-20}$ alkylene group which may be branched, and $R^1$ is a group of the following structural formula (A) or (B):

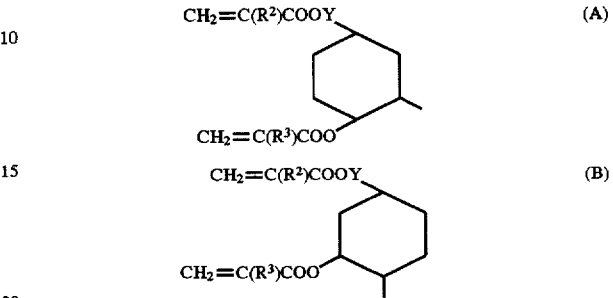

wherein each of $R^2$ and $R^3$ which are independent of each other, is a hydrogen atom or a methyl group, and Y is a $C_{1-6}$ alkylene group which may be branched; a photopolymerizable composition comprising (a) a polymer binder, (b) a photopolymerization initiator, and (c) polymerizable unsaturated group-containing compounds wherein the polymerizable unsaturate group-containing compounds (c) include at least one unsaturated group-containing urethane compound of the above formula (I); and a photosensitive lithographic printing plate employing the photopolymerizable composition as a photosensitive resin layer.

Now, the present invention will be described in detail with reference to the preferred embodiments.

The unsaturated group-containing urethane compound of the present invention is represented by the above formula (I). In the formula, X is a $C_{1-20}$ alkylene group which may be branched, preferably a $C_{2-12}$ alkylene group, more preferably a $C_{4-10}$ alkylene group. Y is a $C_{1-6}$ alkylene group which may be branched, preferably a $C_{1-2}$ alkylene group. The unsaturated group-containing urethane compound of the formula (I) can be prepared in accordance with a known method by a reaction of an organic diisocyanate with a reaction product of the corresponding alicyclic epoxy group-containing acrylate or methacrylate with acrylic acid or methacrylic acid, as shown by the following reaction scheme.

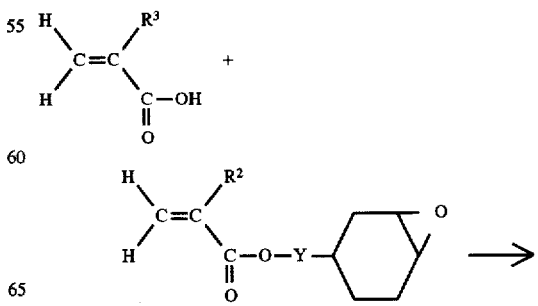

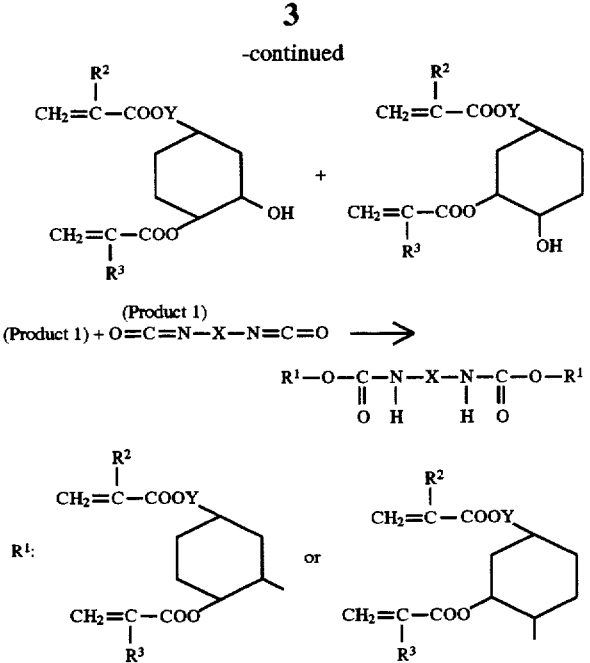

(Product 1)

(Product 1) + O=C=N—X—N=C=O ⟶

$$R^1-O-\underset{\underset{O}{\|}}{C}-\underset{\underset{H}{|}}{N}-X-\underset{\underset{H}{|}}{N}-\underset{\underset{O}{\|}}{C}-O-R^1$$

$R^1$:

In the above formulas, $R^2$, $R^3$ and Y are as defined above.

The reaction of the above first stage can be carried out at a temperature of from 70° to 100° C. in the presence or absence of a solvent using as a catalyst a quaternary ammonium salt such as a tetramethylammonium chloride or benzyltriethylammonium chloride. The reaction of the second stage can be carried out at a temperature of from 60° to 80° C. in an organic solvent such as toluene, benzene or butanone, using as a catalyst an organic metal such as di-butyltin dilaurate.

The compound of the present invention is usually obtainable as a mixture of a compound of the formula (I) wherein $R^1$ is a group of the formula (A) and a compound of the formula (I) wherein $R^1$ is a group of the formula (B). These compounds may be used in the form of the mixture or after being separated.

As the organic diisocyanate to be used in the present invention, various diisocyanates may be mentioned, such as hexamethylene diisocyanate and trimethylhexamethylene diisocyanate.

The compound of the formula (I) of the present invention is useful as a polymerizable monomer for a photopolymerizable composition. Now, the photopolymerizable composition of the present invention will be described.

The photopolymerizable composition of the present invention is characterized in that it contains an urethane compound of the formula (I) as a polymerizable unsaturated group-containing compound (c). The reason why the urethane compound of the present invention exhibits excellent effects, is not clearly understood. However, use of the urethane compound of the present invention is advantageous over the use of other urethane compounds at least with respect to the sensitivity. Further, printing resistance and storage stability will be thereby improved. The content is not particularly limited, but is usually preferably within a range of from 20 to 80 wt %, more preferably from 30 to 70 wt %, based in the total weight of the polymerizable unsaturated group-containing compounds. If the content is less than 20 wt %, the storage stability and the printing resistance tend to be poor, and if it exceeds 80 wt %, the developability tends to be poor. The polymerizable unsaturated group-containing compounds other than the compound of the formula (I) of the present invention, may, for example, be an unsaturated carboxylic acid; an ester of an aliphatic polyhydroxy compound with an unsaturated carboxylic acid; an ester of an aromatic polyhydroxy compound with an unsaturated carboxylic acid; an ester obtainable by an esterification reaction of an unsaturated carboxylic acid and a polybasic carboxylic acid with a polyhydric hydroxy compound such as the above-mentioned aliphatic polyhydroxy compound or an aromatic polyhydroxy compound; or an ester obtainable by an esterification reaction of an unsaturated carboxylic acid with an aliphatic polyhydroxy compound and an aromatic polyhydroxy compound.

Specifically, the unsaturated caboxylic acid may, for example, be acrylic acid or methacrylic acid.

The above-mentioned ester of an aliphatic polyhydroxy compound with an unsaturated carboxylic acid is not particularly limited, and may, for example, be an acrylic acid ester such as ethylene glycol diacrylate, triethylene glycol diacrylate, trimethylol propane triacrylate, trimethylol ethane triacrylate, pentaerythritol diacrylate, pentaerythritol triacrylate, pentaerythritol tetraacrylate, dipentaerythritol tetraacrylate, dipentaerythritol pentaacrylate, dipentaerythritol hexaacrylate or glycerol acrylate, a methacrylic acid ester having "acrylate" in these illustrated compounds substituted by "methacrylate", an itaconic acid ester likewise substituted by "itaconate", a crotonic acid ester likewise substituted by "crotonate", or a maleic acid ester likewise substituted by "maleate".

The ester of an aromatic polyhydroxy compound with an unsaturated carboxylic acid, may, for example, be hydroquinone diacrylate, hydroquinone dimethacrylate, resorcinol diacrylate, resorcinol dimethacrylate or pyrogallol triacrylate.

The ester obtainable by the esterification reaction of an unsaturated carboxylic acid and a polybasic carboxylic acid with a polyhydric hydroxy compound may not necessarily be a single substance. Typical examples include a condensation product of acrylic acid, phthalic acid and ethylene glycol, a condensation product of acrylic acid, maleic acid and diethylene glycol, a condensation product of methacrylic acid, terephthalic acid and pentaerythritol, and a condensation product of acrylic acid, adipic acid, butane diol and glycerol.

The ester obtainable by the esterification reaction of an unsaturated caboxylic acid with an aliphatic polyhydroxy compound and an aromatic polyhydroxy compound, may be an ester compound obtained by reacting two molecules of (meth)acrylic acid to a diol compound, preferably an ester compound obtained by reacting a bisphenol compound or its derivative and two molecules of an aromatic polyhydroxy compound with (meth)acrylic acid. More specifically, it may be a compound of the formula (II):

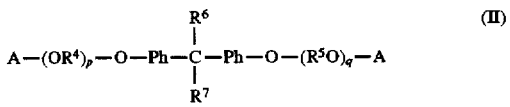

wherein A is an acryloyl group or a methacryloyl group, each of $R^4$ and $R^5$ is an alkylene group which may be branched, each of $R^6$ and $R^7$ is a hydrogen atom, an alkyl group which may be substituted, a cycloalkyl group which may be substituted, or a phenyl group which may be substituted, Ph is a phenylene group and p and q are positive integers satisfying p+q=2 to 30. When the compound of the above formula (II) is used, the sensitivity and the developability will be well balanced and excellent.

More preferred is the one wherein p+q=2 to 4. Specific examples include 2.2-bis[4-(acryloxydiethoxy)phenyl]

propane (A-BPE-4, tradename, manufactured by Shin Nakamura Kagaku Kogyo K.K.), 2,2-bis[4-(methacryloxyethoxy)phenyl]propane (BPE-100, tradename, manufactured by Shin Nakamura Kagaku Kogyo K.K.), and 2,2-bis[4-(methacryloxydiethoxy)phenyl] propane (BPE-200, tradename, manufactured by Shin Nakamura Kagaku Kogyo K.K.).

Now, the photopolymerization initiator (b) as an essential component of the photopolymerizable composition of the present invention will be described. As such a photopolymerization initiator, any initiator may be employed so long as it is capable of initiating polymerization of the above-mentioned polymerizable unsaturated group-containing compounds. Especially the one having a photosensitivity to visible rays can suitably be employed. As an active agent which forms active radicals by some action with a sensitizer excited by light, a hexaarylbiimidazole, a titanocene compound, a halogenated hydrocarbon derivative, a diaryliodonium salt, or an organic peroxide may, for example, be mentioned. Among them, a system employing a hexaarylbiimidazole or a titanocene compound, is preferred, since the sensitivity, storage stability, adhesion of the coating film to a substrate, etc. are thereby good.

As the hexaarylbiimidazole, various types may be employed, including, for example, 2,2'-bis(o-chlorophenyl)-4,4',5,5'-tetra(p-carboethoxyphenyl)biimidazole, 2,2'-bis(o-chlorophenyl)-4,4',5,5'-tetra(p-carbomethoxyphenyl) biimidazole, 2,2'-bis(o-chlorophenyl)-4,4',5,5'-tetra(p-carbofluorophenyl)biimidazole, 2,2'-bis(o-bromophenyl)-4,4',5,5'-tetra(p-iodophenyl)biimidazole, 2,2'-bis(o-chlorophenyl)-4,4',5,5'-tetra(p-chloronaphthyl)biimidazole, 2,2'-bis(o-chlorophenyl)-4,4',5,5'-tetra(p-chlorophenyl) biimidazole, 2,2'-bis(o-bromophenyl)-4,4',5,5'-tetra(p-chloro-p-methoxyphenyl)biimidazole, 2,2'-bis(o-chlorophenyl)-4,4',5,5'-tetra(o,p-dichlorophenyl) biimidazole, 2,2'-bis(o-chlorophenyl)-4,4',5,5'-tetra(o,p-dibromophenyl)biimidazole, 2,2'-bis(o-bromophenyl)-4,4', 5,5'-tetra(o,p-dichlorophenyl)biimidazole, and 2,2'-bis(o,p-dichlorophenyl)-4,4',5,5'-tetra(o,p-dichlorophenyl) biimidazole.

These hexaarylbiimidazoles may be used with other biimidazoles, as the case requires. Biimidazoles can easily be prepared, for example, by the methods disclosed in Bull. Chem. Soc. Japan, 33, 565 (1960) and J. Org. Chem. 36[16]2262 (1971).

As the titanocene compound, various types may be employed. For example, it may be suitably selected for use among various titanocene compounds disclosed in Japanese Unexamined Patent Publications No. 152396/1984 and No. 151197/1986. More specifically, it may, for example, be dicyclopentadienyl-Ti-dichloride, dicyclopentadienyl-Ti-bisphenyl, dicyclopentadienyl-Ti-bis-2,3,4,5,6-pentafluorophen-1-yl, dicyclopentadienyl-Ti-bis-2,3,5,6-tetrafluorophen-1-yl, dicylcopentadienyl-Ti-bis-2,4,6-trifluorophen-1-yl, dicyclopentadienyl-Ti-bis-2,6-difluorophen-1-yl, dicyclopentadienyl-Ti-bis-2,4-difluorophen-1-yl, dimethylcyclopentadienyl-Ti-bis-2,3,4,5,6-pentafluorophen-1-yl, dimethylcyclopentadienyl-Ti-bis-2,6-difluorophen-1-yl, or dicyclopentadienyl-Ti-bis-2,6-difluoro-3-(pyr-1-yl)-phen-1-yl.

Now, the sensitizer in the photopolymerization initiator will be described. The sensitizer in the present invention is a compound which is capable of effectively generating active radicals under irradiation with visible light rays when it is coexistent with the above described active agent.

Typical examples of such a sensitizer include a triphenylmethane-type leuco dye such as leuco crystal violet or leuco malachite green, and a photo-reducible dye such as erythrocin or eosine Y, as disclosed in e.g. U.S. Pat. No. 3,479,185, an aminophenylketone such as Michler's ketone or aminostyrylketone as disclosed in e.g. U.S. Pat. Nos. 3,549,367 and 3,652,275, β-diketones as disclosed in U.S. Pat. No. 3,844,790, indanones as disclosed in U.S. Pat. No. 4,162,162, ketocumarins as disclosed in Japanese Unexamined Patent Publication No. 112681/1977, aminostyrene derivatives and aminophenylbutadiene derivatives as disclosed in Japanese Unexamined Patent Publication No. 56403/1984, aminophenyl heterocyclic compounds as disclosed in U.S. Pat. No. 4,594,310, julolidine heterocyclic compounds as disclosed in U.S. Pat. No. 4,966,830, and pyromethene type dyes as disclosed in Japanese Unexamined Patent Publication No. 241338/1993.

Further, a coumarin compound of the following formula (III) can suitably be used:

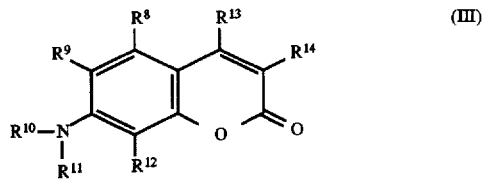

wherein each of $R^8$, $R^9$ and $R^{12}$ is a hydrogen atom, a halogen atom, an alkyl group or an alkoxy group, each of $R^{10}$ and $R^{11}$ is an alkyl group. Otherwise, at least one set of $R^{10}$ and $R^9$, and $R^{11}$ and $R^{12}$, or $R^{10}$ and $R^{11}$, may link to each other to form a substituted or unsubstituted alkylene group. $R^{13}$ is a hydrogen atom, an alkyl group, an acyl group, a cyano group, a carboxyl group or a group of an ester derivative or amide derivative thereof, and $R^{14}$ is a heterocyclic residue having a total number of carbon atoms of from 3 to 17.

Such a coumarin compound can be prepared by a conventional method, for example, by a condensation reaction of an acetic acid ester having a heterocyclic residue with a p-substituted aminosalicyl aldehyde.

In the above formula (III), each of $R^8$, $R^9$ and $R^{12}$ is a hydrogen atom, a halogen atom, an alkyl group or an alkoxy group, preferably a chorine atom, a bromine atom, an iodine atom, a lower alkyl group or a lower alkoxy group, more preferably a hydrogen atom or a $C_{1-4}$ alkyl group. Each of $R^{10}$ and $R^{11}$ is an alkyl group, preferably a $C_{1-16}$ alkyl group which may be branched. Otherwise, at least one set of $R^{10}$ and $R^9$, and $R^{11}$ and $R^{12}$, or $R^{10}$ and $R^{11}$, may link to each other to form a substituted or unsubstituted alkylene group. However, when $R^{10}$ and $R^9$, or $R^{11}$ and $R^{12}$, link to each other to form an alkylene group, such an alkylene group preferably has a carbon number of from 1 to 5. When $R^{10}$ and $R^{11}$ link to each other to form an alkylene group, such an alkylene group preferably has a carbon number of from 3 to 7. Further, the substituent may, for example, be an alkyl group, an alkoxy group, a halogen atom, an aryl group, an acyl group or a carboxyl group. $R^{13}$ is a hydrogen atom, an alkyl group, an acyl group, a cyano group, a carboxyl group or an ester derivative or amide derivative thereof. Among them, a hydrogen atom, a $C_{1-4}$ alkyl group, a $C_{2-5}$ acyl group, a cyano group, a carboxyl group or a $C_{1-5}$ alkyl ester or a $C_{1-5}$ mono- or di-alkylamide thereof, is preferred. $R^{14}$ is a heterocyclic residue having a total number of carbon atoms of from 3 to 17, preferably a nitrogen-containing aromatic heterocyclic residue, more preferably a condensed ring type nitrogen-containing aromatic heterocyclic residue having a total number of carbon atoms of from 3 to 11.

More preferably, a coumarin compound of the following formula (IV) is used.

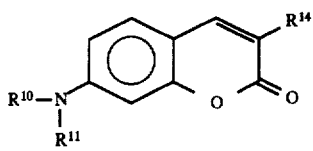

wherein each of $R^{10}$ and $R^{11}$ which are independent of each other, is a $C_{1-16}$ alkyl group which may be branched, or they link to each other to form a $C_{3-7}$ alkylene group, and $R^{14}$ is a heterocyclic residue having a total number of carbon atoms of from 3 to 17.

Specific examples of the substituent represented by $R^{10}$ and $R^{11}$ include a methyl group, an ethyl group, a propyl group, an isopropyl group, a butyl group, a s-butyl group, an isobutyl group, a t-butyl group, a pentyl group, a hexyl group, a heptyl group, an octyl group, a methylpentyl group, a methylhexyl group, an ethylhexyl group and an ethyloxyl group. Further, specific examples of the substituent represented by $R^{14}$ include a thiazolyl group, an oxazolyl group, an imidazolyl group, a benzthiazolyl group, a benzoxazolyl group, and a benzimidazolyl group.

A photopolymerization initiator preferably employed in the present invention, is a combination of the above-mentioned titanocene compound and the coumarin compound. Use of such a combination is particularly advantageous from the viewpoint of the storage stability. Further, such a combination is highly sensitive particularly to visible light.

Now, the polymer binder (a) as an essential component in the photopolymerizable composition of the present invention will be described.

This is a component which imparts a skin-forming ability or a viscosity-regulating ability. Specifically, it may, for example, be a homopolymer or copolymer of (meth)acrylic acid, an ester thereof, maleic acid, acrylonitrile, styrene, vinyl acetate or vinylidene chloride, or polyethylene oxide, polyvinylpyrrolidone, polyamide, polyurethane, polyethylene terephthalate, acetylcellulose or polyvinyl butyral. As a suitable polymer binder, a copolymer containing (meth) acrylic acid and a $C_{1-6}$ alkyl ester of (meth)acrylic acid as copolymer components, may be mentioned. The weight average molecular weight of the polymer binder is usually from 10,000 to 500,000.

Also preferred is a copolymer having the following compound (V) and/or (VI) further incorporated as a copolymer component to such a copolymer:

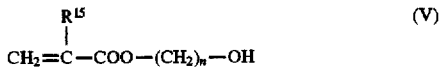

wherein $R^{15}$ is a hydrogen atom or a methyl group, and n is an integer of from 3 to 10.

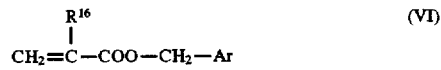

wherein $R^{16}$ is a hydrogen atom or a methyl group, and Ar is a phenyl group which may have a substituent.

In the foregoing, the main constituting components for the photopolymerizable composition of the present invention have been described in detail. Their preferred proportions are such that relative to 100 parts by weight of the polymerizable unsaturated group-containing compounds, in the photopolymerization initiator, the sensitizer is preferably from 0.01 to 20 parts by weight, more preferably from 0.05 to 10 parts by weight, the active agent is preferably from 0.1 to 80 parts by weight, more preferably from 0.5 to 50 parts by weight, and the polymer binder is preferably from 10 to 400 parts by weight, more preferably from 20 to 200 parts by weight.

The photopolymerizable composition of the present invention may contain, in addition to the above-described constituting components, other materials depending upon the particular purpose. For example, a heat polymerization preventing agent such as hydroquinone, p-methoxyphenol or 2,6-di-t-butyl-p-cresol, a coloring agent composed of an organic or inorganic dye or pigment, a plasticizer such as dioctyl phthalate, didodecyl phthalate or tricresyl phosphate, a sensitivity-improving agent such as a tertiary amine or thiol, or other additives such as a colorant precursor, may be incorporated.

Preferred amounts of the above-mentioned various additives are such that relative to 100 parts by weight of the polymerizable unsaturated group-containing compounds, the heat polymerization preventing agent is at most 2 parts by weight, the coloring agent is at most 20 parts by weight, the plasticizer is at most 40 parts by weight, and the colorant precursor is at most 30 parts by weight.

The above-described photopolymerizable composition will be coated, without any solvent or as diluted with a suitable solvent, on a support of e.g. plastic, paper or metal, followed by drying to form a photosensitive layer. To be used for a photosensitive lithographic printing plate, an aluminum support having surface roughening and then anodizing treatment applied, may suitably be employed.

As a surface roughening method, a mechanical method or an electrolytic etching method may, for example, be mentioned. The mechanical method may, for example, be a ball polishing method, a brush polishing method, a liquid horning polishing method, or a buff polishing method. Depending upon e.g. the composition of the aluminum material, the above-mentioned various methods may be used alone or in combination.

The electrolytic etching is carried out in a bath containing one or more of inorganic acids such as phosphoric acid, sulfuric acid, hydrochloric acid and nitric acid. After the surface roughening, desmatte treatment is carried out by means of an aqueous alkaline or acidic solution for neutralization, as the case requires, followed by washing with water.

The anodizing treatment is carried out by electrolysis using an aluminum plate as an anode and a solution containing one or more acids such as sulfuric acid, chromic acid, oxalic acid, phosphoric acid and malonic acid, as an electrolyte. The amount of the formed anodized film is usually from 1 to 50 $mg/dm^2$.

The pore-sealing treatment may, for example, be boiling water treatment, steam treatment, sodium silicate treatment or treatment with an aqueous dichromate solution. As the coating method, a conventional method such as dip coating, rod coating, spin coating, spray coating or roll coating, may be employed.

Further, an oxygen-shielding layer may be formed on the photosensitive layer to prevent the polymerization inhibition action by oxygen. Such a layer may, for example, be made of a water-soluble polymer such as polyvinyl alcohol, polyvinyl pyrrolidone, polyethylene oxide or cellulose. Among them, polyvinyl alcohol having an oxygen gas barrier property is particularly preferred.

The light source for exposure applicable to the composition of the present invention is not particularly limited. However, carbon arc, a high pressure mercury lamp, a xenon lamp, a metal halide lamp, a fluorescent lamp, a tungsten lamp, a halogen lamp, a helium cadmium laser, an argon ion layer, a YAG laser or a helium neon layer may, for example, be particularly suitably used.

The photopolymerizable composition of the present invention is capable of forming an image on the support, if image exposure is carried out with such a light source, followed by development by means of, for example, an aqueous solution containing a surfactant and an alkali. Such an aqueous solution may further contain an organic solvent, a buffering agent, a dye or a pigment. A suitable alkali agent may, for example, be an inorganic alkali agent such as sodium silicate, potassium silicate, sodium hydroxide, potassium hydroxide, lithium hydroxide, sodium tertiary phosphate, sodium secondary phosphate, sodium carbonate, potassium carbonate or sodium hydrogencarbonate, or an organic amine compound such as trimethylamine, diethylamine, monoisopropylamine, n-butylamine, monoethanolamine, diethanolamine or triethanolamine. These compounds may be used alone or in a proper combination. The surfactant may, for example, be a nonionic surfactant such as polyoxyethylenealkylethers, polyoxyethylenealkylallylethers, polyoxyethylenealkylesters, sorbitanalkylesters or monoglycerridealkylesters, an anionic surfactant such as alkylbenzene sulfonates, alkylnaphthalene sulfonates, alkyl sulfates, alkyl sulfonates or sulfosuccinates, or an amphoteric surfactant such as alkylbetaines or amines. Further, as the organic solvent, isopropyl alcohol, benzyl alcohol, ethyl cellosolve, butyl cellosolve, phenyl cellosolve, propylene glycol or diacetone alcohol, may, for example, be incorporated, as the case requires.

Now, the present invention will be described in further detail with reference to Examples and Comparative Examples. However, it should be understood that the present invention is by no means restricted by such specific Examples.

EXAMPLE 1

Preparation of Urethane Compounds 0.1 g of p-methoxyphenol and 0.5 g of tetraethylammonium chloride were added to 17.2 g (0.2 mol) of methacrylic acid, followed by stirring under heating in an oil bath of 75° C. Then, 53.1 g (0.18 mol) of 3,4-epoxycyclohexylmethyl acrylate (A-200, manufactured by Diacel Chemical Industries, Ltd.) was dropwise added thereto over a period of about 2 hours, followed by stirring for three hours. Then, the reaction mixture was washed with dilute sodium bicarbonate and dried over anhydrous magnesium sulfate. The solvent was distilled off to obtain 5.5 g of a slightly yellow oil, which was used by itself for the next reaction.

A mixture comprising 8.4 g of hexamethylene diisocyanate, 15 g of toluene, 10 mg of di-n-butyltin dilaurate and 0.1 g of p-methoxyphenol, was heated to 65° C., and then 30 g of the slightly yellow oil obtained as described above, was dropwise added thereto over a period of about 2 hours. The mixture was stirred under heating for one hour, and then 0.7 ml of methanol was added. The mixture was further stirred under heating for one hour to obtain a mixture of compounds of the following structures. The obtained solution of urethane compounds was used by itself for preparation of a coating liquid of a photopolymerizable composition.

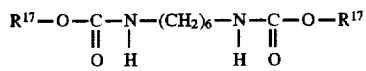

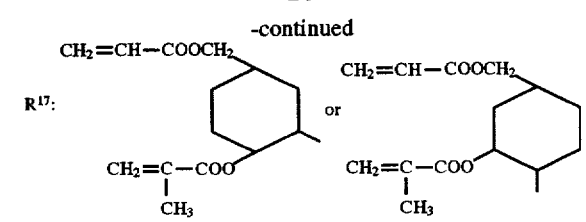

A part of the obtained solution of urethane compounds was sampled and, after distilling off the solvent, examined by $^1$HNMR, whereby a peak corresponding to an olefin (10 H) was observed at 5.5–6.5 ppm, a peak corresponding to methylene of a cyclohexane ring (12 H) was observed at 1.6–2.0 ppm, a peak corresponding to methine adjacent to an oxygen atom, of a cyclohexane ring (4 H) was observed at 4.6–5.2 ppm, and a peak corresponding to methine adjacent to a carbon atom was observed at 2.0–2.2 ppm. Thus, it was confirmed that the desired urethane compounds were formed.

EXAMPLE 2

An aluminum plate was decreased with 3% sodium hydroxide and then subjected to electrolytic etching treatment in a 11.5 g/l hydrochloric acid bath at 25° C. at a current density of 80 A/dm$^2$ for 11 seconds. Then, it was washed with water and then anodized in a 30% sulfuric acid bath at 30° C. at a current density of 11.5 A/dm$^2$ for 15 seconds. Then, it was treated with a 1% sodium orthosilicate aqueous solution at 85° C. for 30 seconds, then washed with water and dried, to obtain an aluminum plate for a lithographic printing plate.

The following photopolymerizable composition coating liquid was coated on the aluminum plate by means of a bar coater so that the dried film thickness would be 2 g/m$^2$ and dried. Further, an aqueous polyvinyl alcohol solution was coated thereon by means of a bar coater so that the dried film thickness would be 3 g/m$^2$, and dried to obtain a photosensitive lithographic printing plate. The photosensitive lithographic printing plate was evaluated with respect of the following evaluation items. The results are shown in Table 1.

| Photopolymerizable composition coating liquid-1 | |
|---|---|
| Urethane compounds of Example 1 | 25 parts by weight |
| A-BPE-4 (tradename, manufactured by Shin Nakamura Kagaku Kogyo K.K.) (The structure as identified below) | 25 parts by weight |
| Methyl methacrylate/methacrylic acid copolymer (acid value: 100, molecular weight: 35,000) | 50 parts by weight |
| Coumarin compound A-1 having a structure as identified below | 2.0 parts by weight |
| Titanocene compound B-1 having a structure as identified below | 2.0 parts by weight |
| 2-Mercaptobenzotianole | 5.0 parts by weight |
| Copper phthalocyanine pigment | 3.0 parts by weight |
| Methyl ethyl ketone | 900 parts by weight |

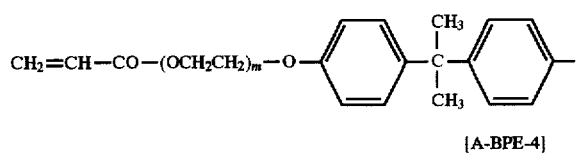

[A-BPE-4]

-continued

Photopolymerizable composition coating liquid-1

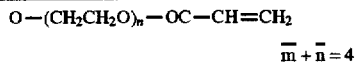

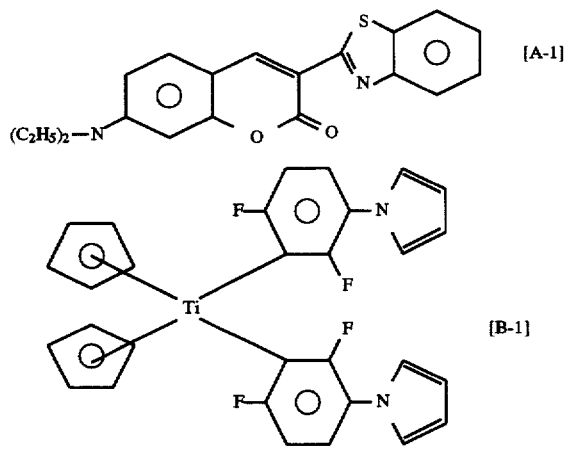

Evaluation Items (1) Sensitivity

The photosensitive lithographic printing plate was exposed by means of a diffraction spectral irradiation apparatus (RM-23, manufactured by Narumi K.K.) and then developed with a developing solution prepared by diluting a developer stock solution comprising 20 wt % of potassium hydroxide, 75 wt % of potassium silicate and 5 wt % of sodium alkylnaphthalene sulfonate (Perex NBL, tradename, manufactured by Kao Corporation), five times with water (i.e. the plate was dipped in the developing solution at 25° C. for 30 seconds and then rubbed 5 times with sponge). From the height of the cured image thereby obtained, the light energy required for the photocuring by light rays with a wavelength of 488 nm, was determined.

(2) Storage stability

From 50 cm above a photosensitive lithographic printing plate stored at 55° C. for 120 hours, light rays with a wavelength of from 480 to 490 nm obtained by a 500 W xenon lamp ("UXL-500DO", tradename, manufactured by Ushio Denki K.K.) through a glass filter ("Y-47" "KL-49", tradename, manufactured by Toshiba. Glass K.K.) were irradiated, and then development was carried out with the above-mentioned developing solution. Then, one drop of methylcellosolve was dropped on a non-image portion of the obtained sample plate and dried, whereupon inking was made with an image-forming ink PI-2 ("SPO-1", tradename, manufactured by Konica K.K.) until the image portion was completely inked.

Symbol ○ indicates that the ink did not attach at all to the non-image portion, symbol △ indicates that the ink slightly attached along the fringe of the dropped methylcellosolve, and symbol X indicates that the ink attached to the entire area of the non-image portion.

(3) Adhesion to the support

The adhesion was evaluated by printing resistance of a photosensitive lithographic printing plate. Specifically, scanning exposure was carried out with an exposure of 100 μj/cm² by an air-cooled argon ion laser of 75 mW, followed by development with the above-mentioned developing solution. The obtained printing plate was subjected to printing by a "Heidelberger GTO" printing machine, whereby the number of printed sheets until the image-portion (120 lines, 4% of small dots) started to scatter, was counted.

COMPARATIVE EXAMPLE 1

A photopolymerizable composition coating liquid was prepared and evaluated in the same manner as in Example 2 except that "urethane compounds of Example 1" in photopolymerizable composition coating liquid-1 was changed to a urethane compound UA-306H (manufactured by Shin Nakamura Kagaku Kogyo K.K.) having a structure as identified below.

The results are shown in Table 1.

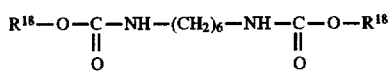

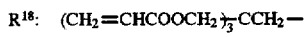

COMPARATIVE EXAMPLE 2

A photopolymerizable composition coating liquid was prepared and evaluated in the same manner as in Example 1 except that "urethane compounds of Example 1" in photopolymerizable composition coating liquid-1 was changed to a urethane compound U-4HA (manufactured by Shin Nakamura Kagaku Kogyo K.K.) having a structure as identified below. The results are shown in Table 1.

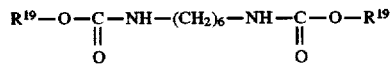

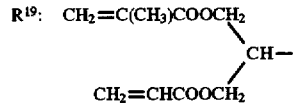

EXAMPLE 3

A photopolymerizable composition coating liquid was prepared and evaluated in the same manner as in Example 2 except that the methyl methacrylate/methacrylic acid copolymer in photopolymerizable coating liquid-1 was changed to methyl methacrylate/isobutyl methacrylate/ methacrylic acid/isobutyl acrylate/4-hydroxybutyl acrylate/ benzyl methacrylate=30/30/15/10/10/5 (mol %), MW 50,000. The results are shown in Table 1.

TABLE 1

|  | Example 2 | Comparative Example 1 | Comparative Example 2 | Example 3 |
|---|---|---|---|---|
| Sensitivity (μj/cm²) | 100 | 200 | 100 | 80 |
| Storage stability | ○ | ○ | X | ○ |
| Printing resistance (× 10,000 sheets) | 5.0 | 1.0 | 3.0 | 5.0 |

The unsaturated group-containing urethane compound of the present invention is useful as a polymerizable monomer for a photopolymerizable composition, and a photopolymerizable composition of the present invention is excellent, when it is used for a photosensitive lithographic printing plate, in all of the sensitivity, storage stability and printing resistance (adhesion to the support), and thus is very useful.

What is claimed is:

1. An unsaturated group-containing urethane compound of the following formula (I):

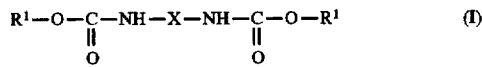

wherein X is a $C_{1-20}$ alkylene group which is branched or unbranched, and $R^1$ is a group of the following structural formula (A) or (B):

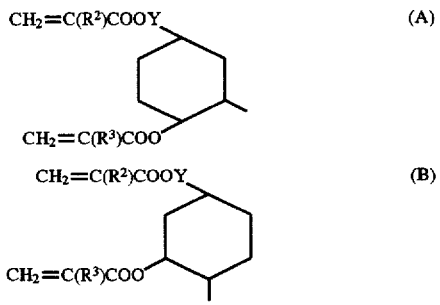

wherein each of $R^2$ and $R^3$ which are independent of each other, is a hydrogen atom or a methyl group, and Y is a $C_{1-6}$ alkylene group which is branched or unbranched.

2. A photopolymerizable composition comprising (a) a polymer binder, (b) a photopolymerization initiator, and (c) polymerizable unsaturated group-containing compounds, wherein the polymerizable unsaturated group-containing compounds (c) include at least one unsaturated group-containing urethane compound as defined in claim 1.

3. The photopolymerizable composition according to claim 2, which contains the unsaturated group-containing urethane compound in an amount of from 20 to 80 wt % based on the total weight of the polymerizable unsaturated group-containing compounds (c).

4. The photopolymerizable composition according to claim 2, which further contains at least one compound of the following formula (II), as the polymerizable unsaturated group-containing compounds:

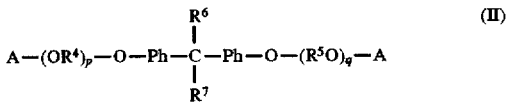

wherein A is an acryloyl group or a methacryloyl group, each of $R^4$ and $R^5$ is an alkylene group which is branched or unbranched, each of $R^6$ and $R^7$ is a hydrogen atom, an alkyl group which is optionally substituted, a cycloalkyl group which is optionally substituted, or a phenyl group which is optionally substituted, Ph is a phenylene group, p and q are positive integers satisfying p+q=2 to 30.

5. The photopolymerizable composition according to claim 2, wherein the photopolymerization initiator (B) comprises a sensitizer showing absorption of visible rays, and a radical forming agent.

6. The photopolymerizable composition according to claim 5, wherein the sensitizer is a coumarin compound.

7. The photopolymerizable composition according to claim 2, wherein the photopolymerization initiator is a titanocene compound.

8. The photopolymerizable composition according to claim 2, wherein the polymer binder is a copolymer containing (meth)acrylic acid and a $C_{1-6}$ alkyl ester of (meth) acrylic acid, as copolymer components.

9. A photosensitive lithographic printing plate having a photosensitive resin layer formed on an aluminum substrate treated by surface roughening and anodizing treatment and, optionally, further by hydrophilic treatment, wherein the photosensitive resin layer is made of the photopolymerizable composition as defined in claim 2.

* * * * *